United States Patent
Wernicke et al.

(10) Patent No.: US 6,756,197 B1
(45) Date of Patent: Jun. 29, 2004

(54) COLLAGENASE 3 AS A PROGNOSTIC MARKER FOR RHEUMATOID ARTHRITIS

(75) Inventors: Dirk Wernicke, Berlin (DE); Erika Gromnica-Ihle, Berlin (DE); Dirk Freudiger, Berlin (DE); Claudia Schulze Westhoff, Berlin (DE)

(73) Assignee: Max-Delbrück-Centrum für Molekulare Medizin, Berlin (DE)

( * ) Notice: Subject to any disclaimer, the term of this patent is extended or adjusted under 35 U.S.C. 154(b) by 0 days.

(21) Appl. No.: 09/979,507

(22) PCT Filed: Mar. 24, 2000

(86) PCT No.: PCT/DE00/00881

§ 371 (c)(1),
(2), (4) Date: May 6, 2002

(87) PCT Pub. No.: WO00/58502

PCT Pub. Date: Oct. 5, 2000

(30) Foreign Application Priority Data

Mar. 25, 1999 (DE) .......................................... 199 13 428

(51) Int. Cl.[7] ................................................. C12Q 1/00
(52) U.S. Cl. ............................................. 435/4; 435/23
(58) Field of Search ............................. 435/4, 7.1, 23, 435/69.2

(56) References Cited

U.S. PATENT DOCUMENTS

| 6,143,506 A | * | 11/2000 | Golub et al. .................. 435/7.1 |
| 6,271,014 B1 | * | 8/2001 | De Saint-Vis et al. ...... 435/226 |
| 6,399,371 B1 | * | 6/2002 | Falduto et al. .............. 435/325 |
| 2002/0099004 A1 | * | 7/2002 | Lund et al ..................... 514/2 |

FOREIGN PATENT DOCUMENTS

| JP | 08-226918 | * | 9/1996 | |
| JP | 2864219 B2 | * | 3/1999 | ........... C12N/15/02 |
| WO | WO 98/29560 A1 | | 7/1998 | |
| WO | WO 98/29560 A1 | | 9/1998 | |

OTHER PUBLICATIONS

Wernicke, D. et al. "Cloning of Collagenase 3 from the Synovial Membrane and its Expression in Rheumatoid Arthritis and Osteoarthritis" The Journal of Rheumatology, vol. 23, No. 4, pp. 590–595, 1996.*

Reboul, P. et al. "The New Collagenases, Collagenase 3, Is Expressed and Synthesized by Human Chondrocytes but not by Synoviocytes" Journal of Clinical Investigation, vol. 97 No. 9, pp. 2011–2019, 1996.*

Pendas, A.M. et al. "Structural Analysis and Promoter Characterization of the Human collagenase–3 Gene (MMP13)" Genomics, vol. 40, pp. 222–233, 1997.*

Stahle–Backdahl, M. et al. "Collagenase–3 (MMP–13) is expressed during human fetal ossification and re–expressed in postnatal bone remodeling and in rheumatoid arthritis" Laboratory Investigation, vol. 76, No. 5, pp. 717–728, 1997.*

Lindy, O. et al. "Matrix Metalloproteinase 13 (Collagenase 3) in Human Rheumatoid Synovium" Arthritis and Rheumatism, vol. 40 No. 8, pp. 1391–1399, 1997.*

* cited by examiner

Primary Examiner—Ralph Gitomer
(74) Attorney, Agent, or Firm—Birch, Stewart, Kolasch & Birch, LLP

(57) ABSTRACT

The invention relates to the use of collagenase 3 for detecting destructive diseases of the joints, especially for prognosing the progression of the disease and the genetic predisposition for rheumatoid arthritis.

11 Claims, 3 Drawing Sheets

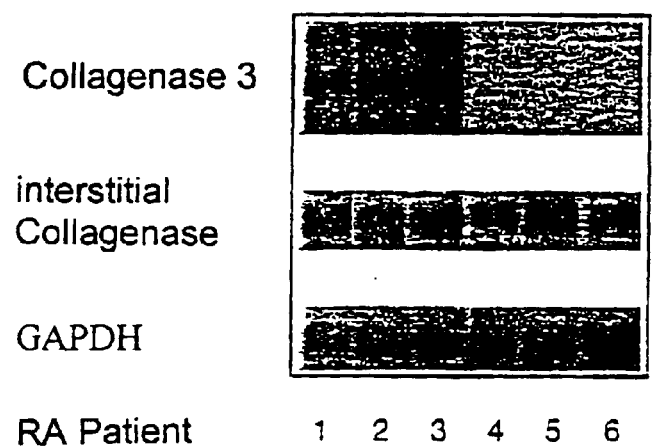
Fig. 1   Northern Blot-Analysis of Collagenase 3 in preparates of synovial membranes of patients with rheumatiod arthritis A
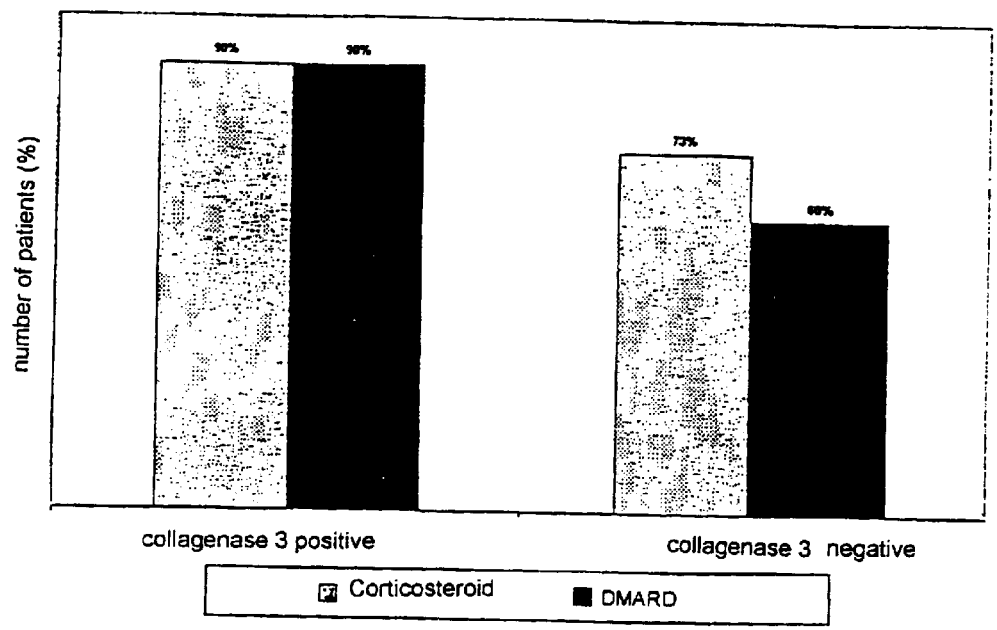
B
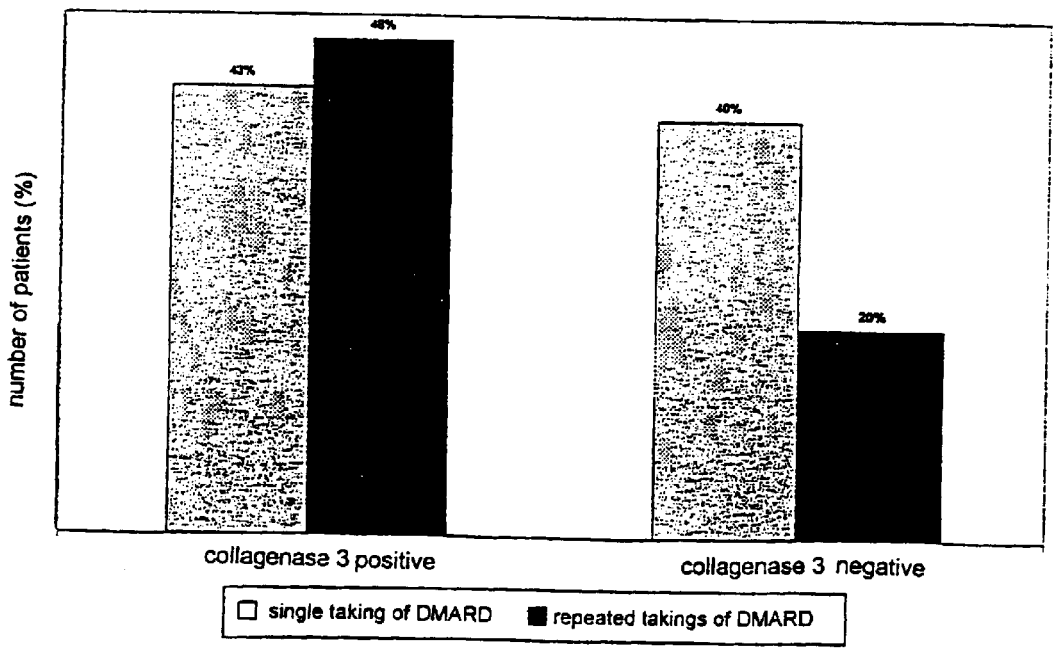
Fig. 2    Therapy with Medicaments

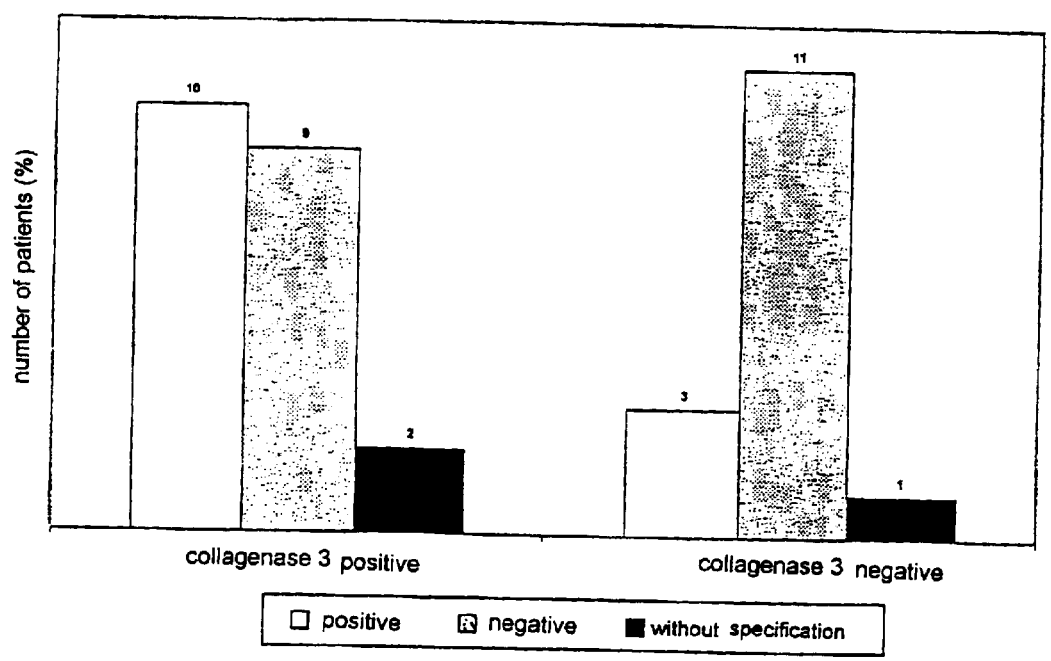
Fig. 3  Anamnesis of familes refer to RA in dependence of Collagenase 3mRNA Expression in the synovial membranes

COLLAGENASE 3 AS A PROGNOSTIC MARKER FOR RHEUMATOID ARTHRITIS

This application is the national phase under 35 U.S.C. § 371 of PCT International Application No. PCT/DE00/00881 which has an International filing date of Mar. 24, 2000, which designated the United States of America.

BACKGROUND OF THE INVENTION

The invention relates to the use of collagenase 3 for detecting destructive joint diseases, especially as a prognostic marker for the clinical course of rheumatoid arthritis (RA) and its genetic predisposition.

RA is a chronically inflammatory disease, predominantly of the joints. The aetiology of the disease as well as relevant pathogenetic mechanisms have remained unknown up to the present. With it being a chronic disease, patients are affected by it for years or decades. The clinical course of the disease is very heterogeneous, changing over the course of the years and decades, and cannot be forecast as yet. An early, adequate forecasting of the progression of the disease to be expected and recognition of the start of a serious progression of the disease in good time are of great importance for the patient and the doctor treating the patient, in order to treat the chronic disease, which has been incurable up to now, efficiently at least in the early stages and thus to decelerate or stop a progression as early as possible. This particularly relates to the stoppage of the process of the progredient cartilage and bone destruction.

Medicinal therapies available at present are effective, albeit frequently connected with serious side-effects. This is connected both with the effective mechanism of the medications themselves, simultaneous combined administration and the necessity of a life-long therapy for years and decades. Currently, combination therapies of (a) steroid preparations (b) immune suppressiva and cytostatics, so-called disease-modifying anti-rheumatic drugs (DMARD, so-called basic therapeutics) and (c) non-steroidal anti-inflammatory medications are in use.

On the Heterogeneity and Pathogenesis of RA

RA is a chronically inflammatory disease characterized by a high degree of heterogeneity, which affects the pattern of the disease, the capability of reacting to therapeutic measures (internal and surgical) and the prognosis of the disease. The clinical heterogeneity is associated with a variety of histo-pathological alterations in the synovial membrane of the joints affected. This clinical and histo-pathological heterogeneity of the disease, combined with insufficient knowledge about aetiology and relevant pathogenetic mechanisms, have led to very insufficient treatment results of RA patients up to now. Within the first two years after the on-set of the disease, about one-third of the RA patients have to give up their professional activity. In internal medicine/rheumatological departments, the share of RA patients is above 50%, in institutions of orthopaedic rheumatology even about 75%. The expenditure for long-term medicinal therapies and stationary therapeutic measures are above-average. The prevalence of the disease amounts to about 1% in the overall population. The pathogenetic measures in the joints affected include a chronic inflammation, an abnormal immune response and a hyperplasia of the synovial membrane. The chronically inflammatory and hyperplastic synovial membrane invades into neighbouring cartilage and bone structures, thus leading to a progredient joint destruction. The clinical end point of the disease is decisively determined by the cartilage and bone destruction, which lead to a loss of function of the joints and to invalidity. However, the anti-inflammatory therapy currently in the foreground of medical therapies only has a low influence on the progression of the cartilage and bone destruction. There are indications for the fact that chronic inflammation and progredient cartilage and bone destruction are rather to be regarded as two separate pathophysiologic entities in a common pathogenetic process.

Prognostic markers available or known up to now for the progression of RA (1) The currently safest markers used in routing in clinical practice for the progression of RA are systemic inflammation parameters such as the erythrocyte sedimentation rate, above all the C-reactive protein (CRP) and, with limitations, other acute-phase proteins. These parameters correlate best with the current acute inflammatory activity in the organism and are the decisive parameters for an anti-inflammatory therapy. As the systemic chronic inflammation and the progredient joint destruction are only conditionally connected with one another pathogenetically, the meaningfulness of these parameters for the prognosis and the progression of the disease is very limited overall, in particular for the progredient cartilage and bone destruction.

(2) The existence of a positive rheumatoid factor is valued as an indicator for a disturbed immune response. However, it is not specific for RA and the meaningfulness for the progression of the disease is limited.

(3) It is further known that certain patterns of antigens which can be detected on the cell surface of lymphocytes and other tissue cells (so-called HLA antigens) are associated with more severe course of RA. Due to the large variety of the HLA antigens and their various epidemiological distribution, comments on the forecast of the RA are only possible in a very limited way. Correlations to the progredient joint destruction were not found.

BRIEF SUMMARY OF THE INVENTION

Reliable prognostic markers of the disease are thus decisive for an early adequate medical treatment and the justification of such a therapy with regard to the side-effects also to be considered.

Therefore, the invention was based on the task of finding corresponding reliable parameters and providing corresponding markers which are particularly suited for RA.

The invention is based on the knowledge that collagenase 3 is involved in the process of progredient cartilage and bone destruction. For the progredient cartilage and bone destruction in RA, various proteases, but above all the matrix metalloprotcinases (MMPs) are responsible, these being able to cleave various components of the extra-cellular matrix. Collagenase 3 as a representative of the MMP family is of particular interest for the cartilage and bone destruction in destructive joint diseases, such as RA. On the one hand, collagenase 3 possesses a high catalytic activity towards collagen type II, the main collagen component of hyaline cartilage, compared with other human collagenases and other MMP's, and cleaves a broad range of other components of the extra-cellular matrix with high efficiency. On the other hand, it has been shown that collagenase 3 can only be detected in adult human tissues under pathological conditions, for example in the growth of malignant tumours, in chronic wounds, as well as in arthritic cartilage and in the synovial membrane in RA. It can therefore be presupposed that this MMP plays a decisive role in the progredient cartilage and bone destruction, in particular also in RA, due to the substrate specificity and the expression pattern of collagenase 3.

An increased concentration of various MMPs was detected in the synovial fluid of RA patients. However, a correlation to systemic inflammation parameters such as BSG and CRP was only shown for stromelysin 1. In addition, no correlation was detected between the collagenolytic activity in the synovial fluid and the degree of cartilage and bone destruction.

In the invention, collagenase 3 is used as a prognostic marker in destructive diseases of the joints, preferably for the detection of a progression of RA.

BRIEF DESCRIPTION OF THE DRAWINGS

FIG. 1 shows mRNA expression of collagenase 3 in the synovial membrane preparations of patients by Northern Blot analysis;

FIGS. 2A and 2B show results of therapy with medicaments in patients with collagenase 3 mRNA expression in the synovial membrane; and FIG. 3 shows rheumatological family anamnesis with regard to RA.

DETAILED DESCRIPTION OF THE INVENTION

With regard to the chronic and changing progression of the disease, the determination of collagenase 3 is used both for prognosis in the first diagnosis and also for the control of the progression of the diseases, in order, inter alia, to recognise the inception of active phases of the disease at an early stage. More serious progressions or more active phases of RA mean both a higher inflammatory activity of the patients (measured above all with the systemic inflammation parameters BSG and CRP) as well as, in particular in this case, a quicker, i.e. more progredient cartilage and bone destruction (measured inter alia by the radiological determination of the Larsen Index, MRT measurements etc.).

Collagenase 3 is intended for this both in tissues (synovial membrane preparations, cartilage and bone preparations, preparations of the synovial membrane/cartilage interface, obtained in synovectomies, artificial joint replacements, inter alia operative interventions, as well as by biopsies) and in body fluids (synovial fluid, blood).

Preferably, the following determinations of collagenase 3 are carried out:

(a) qualitative and quantitative determination of the mRNA expression, inter alia by reverse transcription—polymerase chain reaction (RT-PCR)—analysis, Northern Blot analysis, (b) qualitative and quantitative determination of collagenase 3 antigen (both as a pro-enzyme and also as an activated form), inter alia by Western Blot analysis, immunological detection methods etc., (c) detection of the catalytic activity of the activated collagenase 3, inter alia by zymography, the detection of specific cleaved peptides etc., (d) detection of a disturbed quantitative relationship between collagenase 3 and its specific (tissue-specific inhibitors of MMPs) or unspecific inhibitors ($\alpha$2-macroglobulin etc.) by the determination of free collagenase 3 protein and of the same bound in complexes with inhibitors, inter alia by Western Blot analysis, immunological detection methods etc., (e) detection of collagenase 3 mRNA or antigen in histological preparations of the synovial membrane/cartilage border layer, inter alia by in situ hybridisation or immuno-histochemistry.

In a further embodiment of the invention, collagenase 3 is also used as a potential marker for a genetic predisposition for the disease.

Collagenase 3 can act as a single marker, but can also be evaluated in combination with other markers. Further markers can be those of which either a genetic predisposition is known or presumed or of which it is at least known that they are frequently associated with more severe progressions of the disease (such as certain patterns of HLA antigens, for example HLA-DR4 or the rheumatoid factor).

In combination with other,markers, the prognostic meaningfulness both for the progression of the disease, in particular under the aspect of the progredient cartilage and bone destruction, as well as for the genetic predisposition increases or can obtain a meaning fulness which becomes relevant for clinical practice.

In addition, it has been established that collagenase 3 proenzyme is activated by MT1-MMP and/or gelatinase A. In almost all cases, an mRNA expression of these two other MMPs, membrane type-1 MMP (MT1-MMP) and gelatinase A (MMP-2) takes place at the same time as the mRNA expression of collagenase 3 in synovial membrane preparations of patients with RA. In combination with collagenase 3, MT1-MMP and gelatinase A portray prognostic markers for RA through a determination of their mRNA or protein expression, its amount and localisation or its catalytic activity in tissues or body fluids, as done for collagenase 3.

The invention is explained in more detail below on the basis of embodiments of examples.

Results

Patients 36 patients with a secured diagnosis of RA in accordance with the diagnosis criteria of the American College of Rheumatology of 1987 were included in the examinations. The patients were examined clinically and para-clinically. In all patients, the wrist joints were affected by the disease. In the patients included in the examinations, a rheumatic surgery intervention for the removal of the inflammatory and hyperplastic synovial membrane (so-called synovectomy) in one of the wrist joints in each case was necessary, in order to retard a progression of the joint destruction and to improve the movement capability of the joint. The material removed surgically was both analysed histo-pathologically and also used for the preparation of mRNA. The patients were attended to with regard to internal treatment in the Clinic of Rheumatology in Berlin-Buch and operated in the Orthopaedic Department of the Berlin-Buch Hospital.

mRNA Expression of Collagenase 3 in the Synovial Membrane Preparations

The mRNA expression of collagenase 3 was examined in the synovial membrane preparations of all 36 patients by Northern Blot analysis (FIG. 1). 21 preparations (60%) showed an mRNA expression of collagenase 3. As opposed to this, it is known that the mRNA expression of other MMPs, such as interstitial collagenase and stromelysin 1 is detectable in all synovial membrane preparations (in FIG. 1, only shown for interstitial collagenase). The results of the Northern Blot analysis were confirmed by the examinations with the method of the RT-PCR. It was further found that an mRNA expression of collagenase 3 in synovial membrane preparations of patients with RA is associated in almost all cases with an mRNA co-expression of two other MMPs, membrane type-1 MMP (MT1-MMP) and gelatinase A (MMP-2). If an mRNA expression of MT1-MMP and gelatinase A was detected in the absence of a collagenase 3 mRNA expression, its expression level was distinctly lower than in a expression with collagenase 3 mRNA in the majority of cases. These results were received by Northern Blot analysis and with the method of the RT-PCR (results not shown here).

FIG. 1 shows a representative Northern Blot with synovial membrane preparations from 6 patients with RA. 25 µl total RNA were loaded in each case. Unlike interstitial collagenase, which is expressed in all patients, an mRNA expression of collagenase 3 can only be detected in some of the RA patients. Human glyceraldehyde-3-phosphate dehydrogenase (GAPDH) is used as a control for the application of equivalent amounts of RNA.

Clinical and Para-clinical Parameters

From Table 1, it can be seen that patients with collagenase 3 mRNA expression in the synovial membrane manifest significantly increased systemic BSG ($p<0.05$) and CRP ($p<0.005$) inflammation markers. There are no differences between the two groups of patients with regard to the rheumatoid factor and in the differential haemogram. The degree of cartilage and bone destruction was determined radiologically by means of the Larsen Index by X-rays of the hand, wrist and foot being examined. Although, on the one hand, no significant difference in the degree of bone and cartilage destruction was detected between the two groups of patients with a view to the small cohorte of patients, it was, on the other hand, conspicuous that 24% of the patient group with collagenase 3 mRNA expression in synovial membrane 5 had a time course of the disease of less than 2 years, whereas only one patient (7%) in the group without collagenase 3 mRNA expression had been suffering for less than 2 years. In addition, 6 patients (29%) in the group of patients with collagenase 3 mRNA expression had prior rheumatic surgery interventions in contrast to only 2 patients (14%) in the group of patients without collagenase 3 mRNA expression.

Thus, patients with collagenase 3 mRNA expression in the synovial membrane manifest a higher systemic inflammatory activity and are subjected to rheumatic surgery interventions at a earlier stage (the latter is connected with a more severe progression of the disease and/or with a lower response to medicinal therapies—the second begin discussed in the next point) than patients without collagenase 3 mRNA expression.

TABLE 1

Clinical and para-clinical parameters of RA patients in relation to collagenase 3 mRNA expression in the synovial membrane

| Parameter | Collagenase 3 mRNA expression without | Collagenase 3 mRNA expression with | Statistical analysis |
|---|---|---|---|
| Age, years | 59.6 ± 5.6 (from 32 to 81) | 58.6 ± 4.9 (from 28 to 83) | n.s. |
| Sex (m/f), years | 3/12 | 3/18 | n.s. |
| Length of disease, years | 11.3 ± 3.1 | 10.9 ± 1.8 | n.s. |
| Haemoglobin, mg/dl | 8.3 ± 0.4 | 7.8 ± 0.3 | n.s. |
| Leukocyte count | 9.3 ± 1.1 | 10.3 ± 0.7 | n.s. |
| BSG (mm/h) | 27.0 ± 5.0 | 39.0 ± 5.4 | $p < 0.05$ |
| CRP (mg/l) | 9.2 ± 2.7 | 30.9 ± 6.0 | P y 0.005 |
| Rheumatoid factor positive/ Number of patients (%) | 9/15 (60%) | 14/21 (66%) | n.s. |

Medicinal Therapy

In accordance with the higher systemic inflammation activity in patients with collagenase 3 mRNA expression in the synovial membrane, the latter was treated more frequently with Prednisolon (FIG. 2A). In addition, 15 patients (71%) with collagenase mRNA 3 expression in the synovial membrane were receiving at least 5 mg/ml Prednisolon as compared with 7 patients (47%) without collagenase 3 mRNA expression at the time of the synovectomy. Therapy with DMARD was carried out as single drug therapy. DMARD were prescribed and changed in the following order (matching the aggressiveness of their effect): Chloroquin (250 mg/d), Sulfasalazin (2 g/d), Methotrexat (15–20 mg/week), gold sodium thiomalate (50 mg/week) and Azathioprin (2 mg/kg/d). As shown in FIG. 2A, patients with collagenase 3 mRNA expression in the synovial membrane were treated more frequently with DMARD. In addition, the DMARD had to be changed more frequently due to a lack of efficacy in patients with collagenase 3 mRNA expression in the synovial membrane (FIG. 2B). In both groups of patients, the DMARD had to be changed for two patients per group due to side-effects.

Thus, patients with collagenase 3 mRNA expression in the synovial membrane were treated more aggressively with medications and were more resistant to an effective medical treatment. The latter possibly also led to an earlier necessity of a rheumatism-surgery intervention.

Rheumatological Family Anamnesis with Regard to RA

In the collagenase 3 positive group of patients, 10 of 19 patients (48%) manifested a positive family anamnesis. In the patient group without collagenase 3 mRNA expression in the synovial membrane, on the other hand, members of the family of only three of 14 cases (20%) suffered from RA (FIG. 3). No information was obtained from a total of three patients. Thus, the accumulation of a positive family anamnesis in the patient group with a collagenase 3 mRNA expression in the synovial membrane is conspicuous.

What is claimed is:

1. A method for prognosis of progression of rheumatoid arthritis (RA) and for the evaluation of clinical course by detecting collagenase 3 as a prognostic clinical marker, which comprises:

contacting tissues or body fluids with a substance that binds to collagenase 3 mRNA or to collagenase 3;

determining an amount of bounded collagenase 3 mRNA or bounded collagenase 3, and correlating the amount of bounded collagenase 3 mRNA or bounded collagenase 3, with an amount of collagenase 3 in the tissue or body fluid.

2. A method for detecting a genetic predisposition for rheumatoid arthritis (RA) by detecting collagenase 3 as a prognostic clinical marker, which comprises:

contacting tissues or body fluids with a substance that binds to collagenase 3 mRNA or to collagenase 3;

determining an amount of bounded collagenase 3 mRNA or bounded collagenase 3, and correlating the amount of bounded collagenase 3 mRNA or bounded collagenase 3, with an amount of collagenase 3 in the tissue or body fluid.

3. The method according to claims 1 or 2, wherein collagenase 3 mRNA expression is determined qualitatively and quantitatively.

4. The method according to claims 1 or 2, wherein collagenase 3, both as a pro-enzyme and also in an activated form, is determined qualitatively and quantitatively.

5. The method according to claims 1 or 2, wherein catalytic activity of activated collagenase 3 is detected.

6. The method according to claims 1 or 2, wherein quantitative relationships between collagenase 3 and specific or unspecific inhibitors are determined by determination of free collagenase 3 protein and of collagenase 3 protein bound in complexes with inhibitors and compared.

7. The method according to claims 1 or 2, wherein synovial membrane preparations, cartilage and bone preparations or preparations of a synovial membrane/cartilage interface, obtained in synovectomies, artificial joint replacement, operative interventions, and also in biopsies are used as tissue.

8. The method according to claims 1 or 2, wherein synovial fluid or blood are used as body fluids.

9. The method according to claims 1 or 2, wherein collagenase 3 is used as a marker for detection of a more severe progression of RA or a marker for detection of an increased genetic predisposition.

10. The method according to claims 1 or 2, wherein collagenase 3 and MT1-MMP and/or gelatinase A are used as prognostic markers by determination of their mRNA or protein expression, their amount and localisation or their catalytic activity in tissues or body fluids.

11. The method of claim 9, wherein the marker is an HLA antigen or a marker having certain patterns of HLA antigens.

* * * * *